(12) United States Patent
Subramaniam et al.

(10) Patent No.: US 8,702,693 B2
(45) Date of Patent: Apr. 22, 2014

(54) APPARATUS AND METHODS FOR SUPPLYING FLUID TO AN ELECTROPHYSIOLOGY APPARATUS

(75) Inventors: Raj Subramaniam, Fremont, CA (US); Paul Roche, San Jose, CA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 975 days.

(21) Appl. No.: 12/705,886

(22) Filed: Feb. 15, 2010

(65) Prior Publication Data

US 2010/0211070 A1 Aug. 19, 2010

Related U.S. Application Data

(60) Provisional application No. 61/153,101, filed on Feb. 17, 2009.

(51) Int. Cl.
*A61B 18/10* (2006.01)
(52) U.S. Cl.
USPC .............................................. 606/40; 604/28
(58) Field of Classification Search
USPC .................. 606/32, 34, 37–42; 604/30–45
See application file for complete search history.

(56) References Cited

U.S. PATENT DOCUMENTS

| | | | |
|---|---|---|---|
| 5,437,662 A | 8/1995 | Nardella | |
| 5,437,664 A * | 8/1995 | Cohen et al. | 606/42 |
| 5,643,197 A | 7/1997 | Brucker et al. | |
| 6,053,912 A | 4/2000 | Panescu et al. | |
| 6,466,818 B1 | 10/2002 | Moaddeb et al. | |
| 6,475,213 B1 | 11/2002 | Whayne et al. | |
| 6,494,202 B2 * | 12/2002 | Farmer | 128/200.23 |
| 6,575,969 B1 | 6/2003 | Rittman, III et al. | |
| 7,115,139 B2 | 10/2006 | McClurken et al. | |
| 7,235,070 B2 | 6/2007 | Vanney | |
| 2002/0107512 A1 | 8/2002 | Edwards | |
| 2002/0115991 A1 | 8/2002 | Edwards | |
| 2003/0208193 A1 | 11/2003 | Van Wyk | |
| 2007/0112341 A1 * | 5/2007 | Edwards et al. | 606/32 |
| 2008/0161793 A1 | 7/2008 | Wang et al. | |

FOREIGN PATENT DOCUMENTS

WO WO 00/51513 A1 9/2000

OTHER PUBLICATIONS

Office Action dated Oct. 4, 2012 is corresponding EP App. Ser. No. 10710480.4.
PCT International Search Report and Written Opinion dated Jun. 24, 2010 for PCT app. Ser. No. PCT/US2010/024236.

* cited by examiner

*Primary Examiner* — Michael Peffley
*Assistant Examiner* — Samantha Good
(74) *Attorney, Agent, or Firm* — Seager, Tufte & Wickhem, LLC

(57) ABSTRACT

Methods and apparatus for supplying fluid during a tissue coagulation procedure.

15 Claims, 4 Drawing Sheets

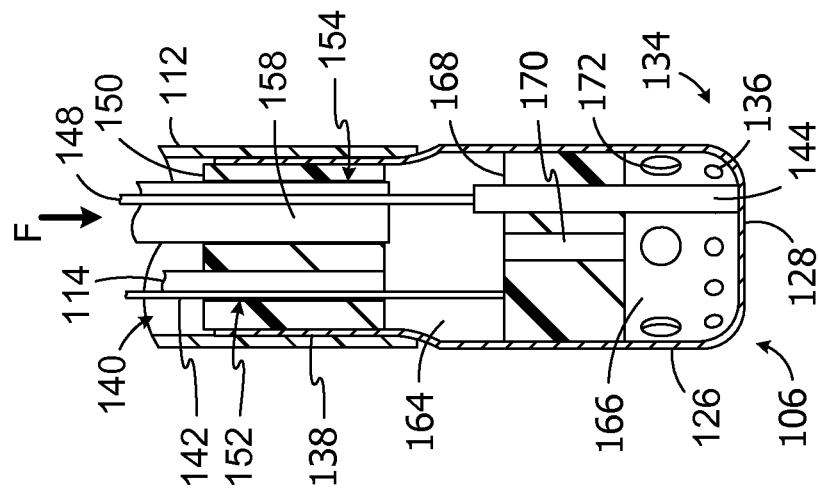
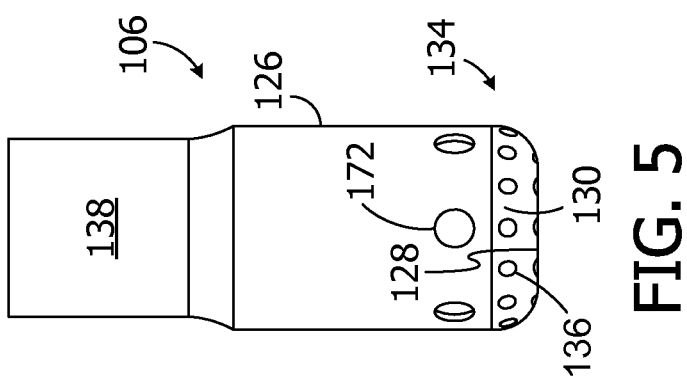
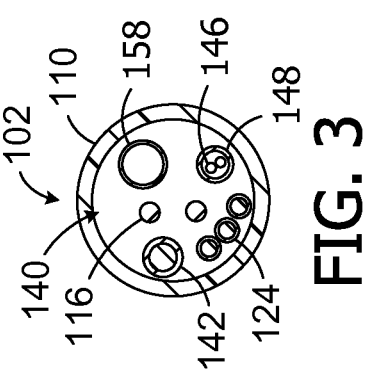
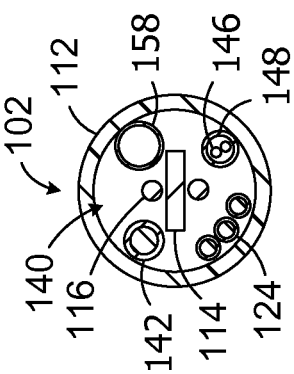

Unit-Based Flow Rate Control

| Rate of Change (°C/Sec.) | Temperature (°C) | | | | | | |
|---|---|---|---|---|---|---|---|
| | 30 | 35 | 40 | 45 | 50 | 55 | 60 |
| -0.3 | -6 | -5 | -4 | -3 | -2 | -1 | BR |
| -0.2 | -5 | -4 | -3 | -2 | -1 | BR | +1 |
| -0.1 | -4 | -3 | -2 | -1 | BR | +1 | +2 |
| 0.0 | -3 | -2 | -1 | BR | +1 | +2 | +3 |
| +0.1 | -2 | -1 | BR | +1 | +2 | +3 | +4 |
| +0.2 | -1 | BR | +1 | +2 | +3 | +4 | +5 |
| +0.3 | BR | +1 | +2 | +3 | +4 | +5 | +6 |

FIG. 7

APPARATUS AND METHODS FOR SUPPLYING FLUID TO AN ELECTROPHYSIOLOGY APPARATUS

CROSS-REFERENCE TO RELATED APPLICATIONS

This application claims the benefit of U.S. Provisional Application Ser. No. 61/153,101, filed Feb. 17, 2009 and entitled "Apparatus And Methods For Supplying Fluid to An Electrophysiology Apparatus," which is incorporated herein by reference.

BACKGROUND

1. Field of the Inventions

The present inventions relate generally to the formation of lesions in tissue.

2. Description of the Related Art

There are many instances where electrodes are inserted into the body. One instance involves the treatment of cardiac conditions such as atrial fibrillation, atrial flutter and ventricular tachycardia, which lead to an unpleasant, irregular heart beat, called arrhythmia. Atrial fibrillation, flutter and ventricular tachycardia occur when anatomical obstacles in the heart disrupt the normally uniform propagation of electrical impulses in the atria. These anatomical obstacles (called "conduction blocks") can cause the electrical impulse to degenerate into several circular wavelets that circulate about the obstacles. These wavelets, called "reentry circuits," disrupt the normally uniform activation of the chambers within the heart.

A variety of minimally invasive electrophysiological procedures, employing catheters and other electrophysiology apparatus that carry one or more electrodes, have been developed to treat conditions within the body by ablating soft tissue (i.e. tissue other than blood and bone). With respect to the heart, minimally invasive electrophysiological procedures have been developed to treat atrial fibrillation, atrial flutter and ventricular tachycardia by forming therapeutic lesions in heart tissue. The formation of lesions by the coagulation of soft tissue (also referred to as "ablation") during minimally invasive surgical procedures can provide the same therapeutic benefits provided by certain invasive, open-heart surgical procedures.

Tissue charring due to overheating, as well as thrombus and coagulum formation, are sometimes associated with soft tissue coagulation. In order to, among other things, prevent tissue charring and thrombus/coagulum formation, while enabling deeper lesion formation, a variety of electrophysiology systems employ fluid to cool the electrode (or electrodes) and/or the tissue adjacent to the electrodes. In some systems, which are sometimes referred to as "open irrigation systems," conductive fluid (e.g. saline) exits the electrophysiology device through outlets in the catheter shaft and/or outlets in the electrode. The conductive fluid cools the electrode and adjacent tissue to prevent charring. The conductive fluid also prevents thrombus formation by diluting the blood that comes into contact with the electrode, and also prevents coagulation of blood on the electrode. In some systems, conductive fluid is supplied to the catheter at a constant and relatively high flow rate (e.g. 20-30 ml/min.) during tissue coagulation. In others, this relatively high flow rate may be increased during the coagulation procedure in order to maintain a preset tissue temperature.

The present inventors have determined that conventional open irrigation systems are susceptible to improvement. For example, the present inventors have determined that conventional open irrigation systems can supply too much conductive fluid to the patient, which is sometimes referred to as "fluid overload," and cause hemodilution or other adverse results.

SUMMARY

Methods and apparatus in accordance with at least some of the present inventions control the fluid flow rate as a function of the measured temperature and the rate of change of the measured temperature without attempting to maintain a constant temperature during a tissue coagulation procedure. Should the measured temperature reach a safety temperature, power supplied to the associated tissue coagulation apparatus is substantially reduced. Such methods and apparatus provides a number of advantages over conventional methods and apparatus. For example, the present methods and apparatus reduce the volume of fluid supplied to the patient.

The above described and many other features and attendant advantages of the present inventions will become apparent as the inventions become better understood by reference to the following detailed description when considered in conjunction with the accompanying drawings.

BRIEF DESCRIPTION OF THE DRAWINGS

Detailed description of exemplary embodiments will be made with reference to the accompanying drawings.

FIG. 3 is a section view take along line 3-3 in FIG. 1.

FIG. 4 is a section view take along line 4-4 in FIG. 1.

FIG. 5 is an elevation view of an electrophysiology electrode in accordance with one embodiment of a present invention.

FIG. 6 is a section view take along line 6-6 in FIG. 1.

FIG. 7 is a table in accordance in accordance with one embodiment of a present invention.

DETAILED DESCRIPTION OF EXEMPLARY EMBODIMENTS

The following is a detailed description of the best presently known modes of carrying out the inventions. This description is not to be taken in a limiting sense, but is made merely for the purpose of illustrating the general principles of the inventions.

The present inventions have application in the treatment of conditions within the heart, gastrointestinal tract, prostrate, brain, gall bladder, uterus, and other regions of the body. With regard to the treatment of conditions within the heart, the present inventions may be associated with the creation of lesions to treat atrial fibrillation, atrial flutter and ventricular tachycardia.

Figure 2:
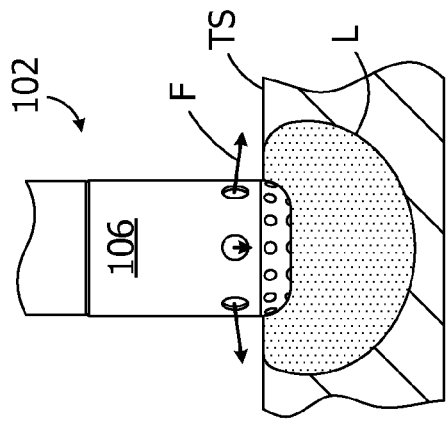
FIG. 2 is a partial section view showing a lesion being formed by the electrophysiology system illustrated in FIG. 1.
Figure 1:
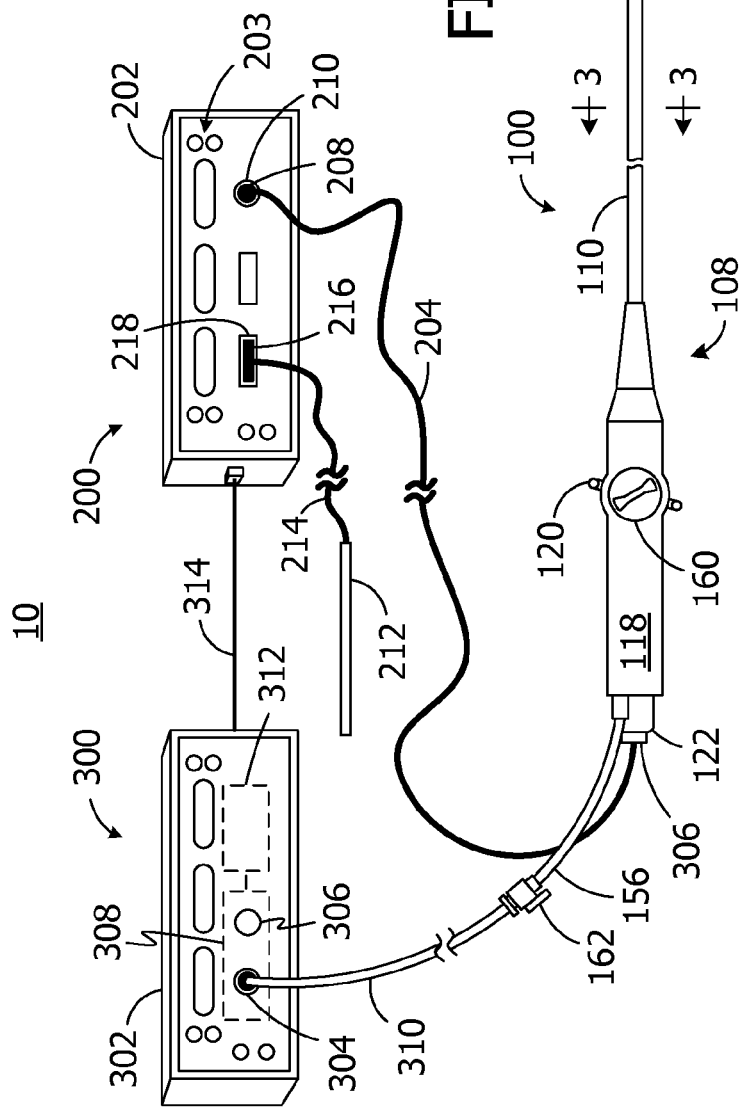
FIG. 1 is a perspective view of an electrophysiology system in accordance with one embodiment of a present invention.

A tissue coagulation system 10 in accordance with one embodiment of a present invention is illustrated in FIG. 1. The exemplary system 10 includes a catheter apparatus 100, a power supply and control apparatus 200, and a fluid supply and control apparatus 300. The tissue coagulation system 10 may be used to perform an open irrigation tissue coagulation procedure, where fluid F exits a tip electrode 106 on the catheter apparatus 100 in the manner illustrated for example in FIG. 2, to create a lesion L in a tissue surface TS. The fluid supply and control apparatus 300 is configured to supply cooling fluid to the catheter apparatus 100 during coagulation procedures in a manner that limits the volume of fluid supplied to the patient. Limiting the volume of cooling fluid may, however, result in temperature increases at the electrode 106 beyond that which is desirable and, accordingly, the power supply and control apparatus 200 may be configured to substantially reduce the power supplied to the electrode 106 if the temperature reaches a threshold (or "safety") temperature. Additional detail concerning the manner in which the present coagulation procedures are performed, including the manner in which power and fluid are supplied, is presented below with reference to FIGS. 7-9. It should also be noted that the system illustrated in FIGS. 1 and 2, and described in greater detail below with further reference to FIGS. 3-6, is merely one example of a tissue coagulation system with which the present inventions may be associated. The present inventions are applicable to any and all open irrigation coagulations systems, including those yet to be developed and those that are not catheter based, as well as to the individual components thereof.

The exemplary catheter apparatus 100 illustrated in FIG. 1 includes a hollow, flexible catheter 102, a plurality of ring electrodes 104, a tip electrode 106, and a handle 108. The catheter 102 may be steerable and formed from two tubular parts, or members, both of which are electrically non-conductive. The proximal member 110 is relatively long and is attached to the handle 108, while the distal member 112, which is relatively short, carries the electrodes 104 and 106. The exemplary catheter 102 is also configured for use within the heart and, accordingly, is about 6 French to about 10 French in diameter and the portion that is inserted into the patient is typically about 60 to 160 cm in length. The exemplary catheter apparatus 100 is steerable and, to that end, is provided with a conventional steering center support and steering wire arrangement. Referring to FIGS. 1, 3 and 4, the proximal end of the exemplary steering center support 114 is mounted near the distal end of the proximal member 110, while the distal end of the steering center support is secured to (but electrically insulated from) the tip electrode 106 in the manner described below. A pair of steering wires 116 are secured to opposite sides of the steering center support 114 and extend through the catheter body 102 to the handle 108, which is also configured for steering. More specifically, the exemplary handle 108 includes a handle body 118 and a lever 120 that is rotatable relative to the handle body. The proximal end of the catheter 102 is secured to the handle body 118, while the proximal ends of the steering wires 116 are secured to the lever 120. Rotation of the lever 120 will cause the catheter distal member 112 to deflect relative to the proximal member 110.

The exemplary ring electrodes 104, which may be used for electrical sensing or tissue coagulation, are connected to an electrical connector 122 on the handle 108 by signal wires 124. Electrically conducting materials, such as silver, platinum, gold, stainless steel, plated brass, platinum iridium and combinations thereof, may be used to form the electrodes 104. The diameter of the exemplary electrodes 104 will typically range from about 5 French to about 11 French, while the length is typically about 1 mm to about 4 mm with a spacing of about 1 mm to about 10 mm between adjacent electrodes.

Turning to FIGS. 5 and 6, the exemplary tip electrode 106 includes a tubular side wall 126, a planar end wall 128 and a curved wall 130 that extends from the side wall to the end wall. The distal region 134 of the tip electrode 106 may have a plurality of surface discontinuities 136. The shape of the planar end wall 128 spreads current over a relatively large tissue contact area, while the surface discontinuities 136 create edge effects and concentrate current adjacent to the outer perimeter of the electrode 106 where the electrode and tissue are being cooled by the fluid flowing from the fluid outlets 172 (discussed below). The proximal region 138 is configured to fit into the catheter lumen 140 and is secured thereto with, for example, adhesive. Power for the tip electrode 106 is provided by a power wire 142 (FIGS. 3, 4 and 6) that is soldered to a portion of the tip electrode and extends through the catheter lumen 140 to the electrical connector 122 on the handle 108. A temperature sensor 144 may be mounted within the electrode 106 and, in the illustrated embodiment, the temperature sensor is a thermocouple. The thermocouple wires 146 extend through a tube 148 to the electrical connector 122.

An anchor member 150 may be mounted within the proximal region 138 of the exemplary electrode 106. The anchor member 150, which may be formed from an electrically conductive material such as stainless steel or an electrically non-conductive material such as nylon or polyimide, includes a pair of lumens 152 and 154. The steering center support 114 is positioned within the lumen 152 and is secured to the anchor member 150. In those instances where the anchor member 150 is electrically conductive, the portion of the steering center support 114 secured thereto may be covered with an electrically non-conductive material. The power wire 142 extends through the lumen 152, while the thermocouple tube 148 extends through the lumen 154.

With respect to the cooling of the tip electrode 106 and adjacent tissue, a fluid inlet tube 156 (FIG. 1) extends into the handle 108 and is connected to a valve (not shown) within the handle. A fluid tube 158 (FIGS. 3, 4 and 6) extends from the valve to the tip electrode 106. A control knob 160 on the handle body 118 is connected to the valve and allows the clinician to, if necessary, control the fluid flow rate through the valve. A connector 162, which may be connected to the fluid supply and control apparatus 300 in the manner described below, is mounted on the proximal end of the fluid tube 156. The distal end of the fluid tube 158 is mounted within the tip electrode 106, which includes a pair of cooling chambers 164 and 166 (FIG. 6) that are separated by a thermal mass 168. Cooling fluid F enters the cooling chamber 164 by way of the fluid tube 158. A fluid lumen 170 in the thermal mass 168 allows fluid to flow from the cooling chamber 164 to the cooling chamber 166. Fluid exits the cooling chamber 166 (and the electrode 106) by way of a plurality of fluid outlets 172 that are aligned with the cooling chamber 166 and extend through the tubular side wall 126.

As for materials and dimensions, the exemplary tip electrode 106 may be formed from any suitable electrically conductive material. By way of example, but not limitation, suitable materials for the main portion of the tip electrode 106 include silver, platinum, gold, stainless steel, plated brass, platinum iridium and combinations thereof. The thermal mass 168 may be formed from electrically and thermally conducting material such as, for example, brass, copper and stainless. The thermal mass 168 may, alternatively, be made of thermally conducting and electrically non-conducing materials, although the power wire 142 will have to be attached to another portion of the tip electrode 106. The tip electrode 106 may be generally cylindrical in shape and, when sized for use within the heart, the tubular side wall 126 may be from about 5 French to about 11 French (about 1.67 mm to about 3.67 mm) in diameter and about 2 mm to about 6 mm in length. The wall thickness may be about 0.05 mm to about 0.3 mm. The diameter of the planar end wall 128 may be about 30% to about 95% of the outer diameter of the tubular side wall 126. The axial length of distal region 134 of the tip electrode 106, i.e. the region that is distal of the fluid outlets, may be about 0.2 mm to about 1 mm. The distal ends of the fluid outlets 172 may be about 0.5 mm to about 2 mm from the end wall 128. The surface discontinuities 136 may be hemispherical-shaped indentations that are about 0.1 mm to about 0.5 mm in depth and diameter, and cover about 30% to about 70% of the associated portion of the electrode surface.

The exemplary power supply and control apparatus ("power supply") 200 includes an electrosurgical unit ("ESU") 202 that supplies and controls RF power. A suitable ESU is the Model 21000TC Maestro 3000 cardiac ablation system sold by Boston Scientific Corporation of Natick, Mass. The ESU 202 has a control panel 203 that allows the user to, for example, set the power level, the duration of power transmission and a safety temperature for a given coagulation procedure. The ESU 202 transmits energy to the electrode 106 by way of a cable 204. The cable 204 includes a connector 206 which may be connected to the catheter electrical connector 122 which, in turn, is connected to the catheter apparatus power and signal wires 124, 142 and 146. The cable 204 also includes a connector 208, which may be connected to a power output port 210 on the ESU 202. Power to the catheter apparatus 100 may be maintained at a constant level during a coagulation procedure, or may be varied, or may substantially reduced or may be shut off completely, depending upon the temperature measured at the tip electrode 106 with the temperature sensor 144. Alternatively, in those instances where temperature sensors are not employed, temperature may be estimated using other parameters.

The exemplary ESU 202 is capable of performing both unipolar and bipolar tissue coagulation procedures. During unipolar procedures performed with the exemplary system 10 illustrated in FIG. 1, tissue coagulation energy emitted by the electrode 106 is returned to the ESU 202 through an indifferent electrode 212 that is externally attached to the skin of the patient with a patch and a cable 214. The cable 214 includes a connector 216 that may be connected to one of the power return ports 218 on the ESU 202. Preferably, the ESU power output port 210 and corresponding connector 208 have different configurations than the power return port 218 and corresponding connectors 216 in order to prevent improper connections.

The exemplary fluid supply and control apparatus ("fluid supply") 300 illustrated in FIG. 1 may be used to supply cooling fluid to the catheter apparatus 100 or other electrophysiology device. The fluid supply 300 includes housing 302, a fluid outlet port 304, a fluid inlet port 306, a reservoir (not shown), and a pump 308 that is connected to the reservoir and the outlet. The fluid outlet port 304 may be coupled to the catheter apparatus connector 162 by a connector tube 310. The fluid inlet port 306 may be connected to a catheter apparatus by a connector tube (not shown) in those instances where some of the cooling fluid is returned to the fluid supply 300. The pump 308 is capable of variable flow rates (e.g. about 1 ml/min to about 70 ml/min). The reservoir may be located within the housing 302, or may be exterior to the housing. The cooling fluid is not limited to any particular type of fluid. In some procedures, the osmolarity of the cooling fluid will be the same as that of blood. In some procedures, the fluid will be an electrically conductive fluid such as saline. A suitable fluid temperature is about 0 to 25° C. and the fluid supply 300 may be provided with a suitable cooling system, if desired, to bring the temperature of the fluid down to the desired level.

The fluid supply 300 also includes a controller 312 that, in the illustrated implementation, receives information such as measured temperature and supplied power from the power supply 200 by way of a connection 314. The connection 314 may be a wired connection, as shown, or may be a wireless connection. The controller 312 controls the flow rate from the pump 308 based on the temperature data received from the power supply 200. The manner in which the controller 312 processes temperature information and derives control signals to control the pump 308 (and flow rate) can vary. For example, the controller 312 can employ proportional control principles, adaptive control, neural network, or fuzzy logic control principles. In the illustrated implementation, proportional integral derivative (PID) control principles are applied.

As noted above, cooling fluid F may be supplied to the catheter apparatus 100 by the fluid supply 300 during an ablation procedure in a manner that limits the volume of fluid supplied to the patient. For example, the flow rate during a coagulation procedure may be controlled (i.e. increased, decreased or maintained as compared to a base flow rate) as a function of the temperature at the tip electrode and the rate of change of temperature at the tip electrode. The control of the cooling fluid flow rate may occur in such a manner that the temperature at the tip electrode is allowed to increase during the coagulation procedure, so long as a predetermined safety temperature is not reached. The safety temperature may be input by the user and may be greater than the tip temperature at which tissue coagulation occurs in an irrigated procedure (about 40° C.) and less than the tip temperature at which desiccation/boiling occurs in an irrigated procedure (about 65° C.). One exemplary safety temperature is 55° C. The power supplied to the tip electrode will remain constant at, for example, a power level input by the user (e.g. 20 watts). If the safety temperature is reached during a coagulation procedure, power to the tip electrode is substantially reduced, i.e. is reduced to a low power level or is shut-off completely by the ESU 202. The low power level may be preset low level (e.g. 5 watts) or a preset low percentage of the input power level (e.g. 50%). In either case, the power level is below that at which tissue will be coagulated.

Changes in the fluid flow rate, as compared to a base flow rate, may be accomplished through unit-based increases and decreases in some implementations. In other words, the magnitude of a particular increase or decrease in flow rate may be one or more predefined units. In one exemplary implementation, each unit is equal to 4 ml/min and, accordingly, a one unit increase would be an increase of 4 ml/min while a two unit decrease would be a decrease of 8 ml/min. The magnitude of the unit will depend upon factors such as electrode tip size, power level and cooling fluid temperature, keeping in mind the goal of lowering the volume of fluid supplied to the patient.

In some procedures, fluid will be supplied at a relatively low maintenance fluid flow rate (e.g. about 1 ml/min.) whenever the catheter 102 is within the patient in order to maintain patency of the fluid path. In some procedures, the rate of fluid flow will be increased to a base rate by the controller 212 when the ESU 202 initiates power delivery to the catheter apparatus 100. One exemplary base rate is 15 ml/min.

One example of the manner in which the controller 212 will control the flow rate, as a function of both temperature and the rate of temperature change, is illustrated in table form FIG. 7. The table displays the unit-based adjustments from the base rate that will occur at various temperatures and temperature rates of change. In the illustrated example, 45° C. is the preferred temperature, i.e. the temperature at which the flow rate will remain at the base flow rate if the temperature is constant (i.e. of rate of change is 0.0). Positive integers are indicative of increases from the base flow rate, negative integers are indicative of decreases from the base flow rate, and "BR" indicates that the flow rate is the base flow rate. The magnitude of the unit-based increase/decrease (if any) at a particular rate of temperature change is based on the difference between the measured temperature and the safety temperature set by the user. For example, where the rate of change is equal to +0.2° C./sec., the flow rate will be set at four units above the base flow rate if the temperature is 55° C., will be set at the base flow rate if the temperature is 35° C., and will be set at one unit below the base flow rate if the temperature is 30° C. Different electrode tip sizes, procedure power levels and/or cooling fluid temperatures could result in a different adjustments than those illustrated in FIG. 7.

The frequency of the unit-based adjustments (if necessary) may vary. In one exemplary implementation, the unit-based adjustments (if necessary) will occur about every 2-5 seconds.

It should also be emphasized again that the present control scheme does not attempt to maintain a set temperature by varying fluid flow. Instead, the present control scheme seeks to prevent the temperature from reaching the safety temperature for the duration of the coagulation procedure while minimizing the volume of fluid supplied to the patient. There are a number of instances where, despite the fact that the measured temperature is relatively high, the flow rate will be the base rate (or less) if the rate of change is sufficiently negative, e.g. at 55° C. with a –0.3° C./sec. rate of temperature change. Additionally, in those instances where the measured temperature is already relatively low but increasing, the flow rate will be held below the base rate if the temperature is not increasing at a high enough rate, e.g. at 30° C. and a +0.1° C./sec. rate of temperature change. The volume of fluid supplied to patient is thereby reduced, as compared to conventional systems that attempt to maintain a set temperature.

Figure 9:
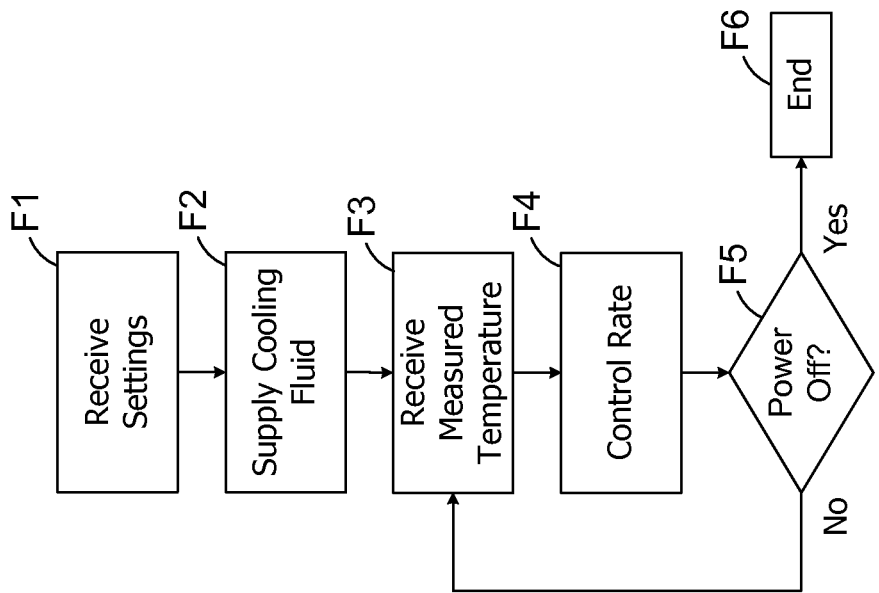
FIG. 9 is a flow chart in accordance with one embodiment of a present invention.
Figure 8:
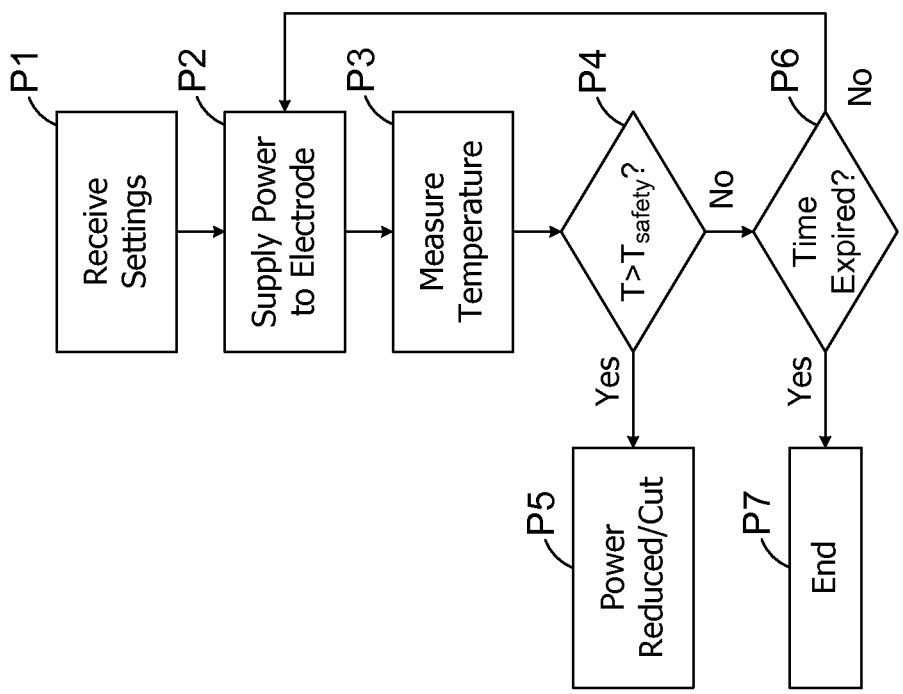
FIG. 8 is a flow chart in accordance with one embodiment of a present invention.

To summarize, and referring to FIGS. 8 and 9, a tissue coagulation procedure in accordance with at least some of the present inventions may proceed as follows. Prior to the initiation of power and fluid, the user inputs various power supply settings, e.g. constant power level, duration and safety temperature, into the power supply 200 (step P1) and inputs various fluid supply settings, e.g. the base rate and the adjustment unit, into the fluid supply 300 (step F1). The constant power level may also be input into the fluid supply 300 by the user, or transmitted from the power supply 200 to the fluid supply. Next, cooling fluid and power will be supplied to the tip electrode 106 (steps P2 and F2). The temperature at the tip electrode 106 is measured by the power supply 200 and is provided to the fluid supply 300 (steps P3 and F3). At the power supply 200, the measured temperature is compared to the input safety temperature (step P4) and, if the measured temperature is greater than input safety temperature, power will be substantially reduced or cut-off (steps P5). Flow rate will drop will be adjusted in the manner described above with reference to FIG. 7 when the power is substantially reduced, and the flow rate will drop to the maintenance rate when the power is cut-off. If the measured temperature is not greater than input safety temperature, the power will continue to be supplied until the preset time limit has expired (steps P6 and P7) or the user manually ends the procedure. At the fluid supply 300, the temperature and rate of temperature change are used to control the rate that fluid is supplied in the manner described above (step F4). This will continue until the power supply 200 ends the coagulation procedure (steps F5 and F6), at which time the flow rate will drop to the maintenance rate.

Although the present inventions have been described in terms of the preferred embodiments above, numerous modifications and/or additions to the above-described preferred embodiments would be readily apparent to one skilled in the art. By way of example, but not limitation, catheter apparatus may be configured such that some of the cooling fluid is returned to the fluid source by way of a second fluid tube. The present inventions are also applicable to surgical probes with relatively short shafts, as well as systems that employ multiple electrodes to transmit coagulation energy to tissue. Also, the functionality of a power supply and control apparatus 200 and a fluid supply and control apparatus 300 may be incorporated into a single apparatus. It is intended that the scope of the present inventions extend to all such modifications and/or additions and that the scope of the present inventions is limited solely by the claims set forth below.

We claim:

1. A method of coagulating tissue, comprising the steps of:
supplying power to a tissue coagulation apparatus at a constant power rate;
supplying fluid to the tissue coagulation apparatus at a fluid flow rate that is equal to a base fluid flow rate;
measuring a temperature at the tissue coagulation apparatus;
determining a rate of temperature change;
adjusting the fluid flow rate from the base fluid flow rate as a function of predetermined combinations of both the measured temperature and the rate of change of the measured temperature without attempting to maintain a constant temperature; and
substantially reducing the power supplied to the tissue coagulation apparatus when the measured temperature is at least equal to an input safety temperature.

2. A method as claimed in claim 1, wherein the step of adjusting the fluid flow rate comprises adjusting the fluid flow rate through a number of unit increases from the base fluid flow rate, or a number of unit decreases from the base fluid flow rate.

3. A method as claimed in claim 2, wherein the number of unit increases is inversely proportional to a difference between the measured temperature and the input safety temperature.

4. A method as claimed in claim 2, wherein the number of unit decreases is proportional to a difference between the measured temperature and the input safety temperature.

5. A method as claimed in claim 1, wherein the base fluid flow rate is about 15 ml/min.

6. A method as claimed in claim 1, wherein the step of substantially reducing the power supplied comprises ending the step of supplying power to the tissue coagulation apparatus in response the measured temperature being at least equal to the input safety temperature.

7. A method as claimed in claim 1, wherein the
the tissue coagulation apparatus includes an electrode; and
the step of measuring temperature comprises measuring temperature at the electrode.

8. A method as claimed in claim 7, wherein the tissue coagulation apparatus includes at least one fluid outlet.

9. A method as claimed in claim 8, wherein the electrode includes the at least one fluid outlet.

10. A method as claimed in claim 1, wherein the step of adjusting the fluid flow rate comprises selectively increasing, decreasing and maintaining the fluid flow rate as a function of the measured temperature and the rate of change of the measured temperature without attempting to maintain a constant temperature.

11. A method as claimed in claim 10, wherein at a predetermined measured temperature, the fluid flow rate is increased in response to a first rate of change of the measured temperature, the fluid flow rate is decreased in response to a second rate of change of the measured temperature, and the fluid flow rate is maintained in response to a third rate of change of the measured temperature.

12. A method as claimed in claim 10, wherein at a predetermined measured temperature, the fluid flow rate is increased in response to a first positive rate of change of the measured temperature and the fluid flow rate is decreased in response to a second positive rate of change of the measured temperature.

13. A method as claimed in claim 1, wherein the step of adjusting the fluid flow rate comprises
adjusting the fluid flow rate from the base fluid flow rate by a first non-zero amount at a first measured temperature and a first rate of change of the measured temperature without attempting to maintain a constant temperature; and
adjusting the fluid flow rate from the base fluid flow rate by a second non-zero amount, the second non-zero amount being different than the first non-zero amount, at the first measured temperature and a second rate of change of the measured temperature, the second rate of change being different than the first rate of change, without attempting to maintain a constant temperature.

14. A method of coagulating tissue, comprising the steps of:
supplying power to a tissue coagulation apparatus at a constant power rate;
supplying fluid to the tissue coagulation apparatus at a fluid flow rate that is equal to a base fluid flow rate;
measuring a temperature at the tissue coagulation apparatus;
determining a rate of temperature change;
adjusting the fluid flow rate from the base fluid flow rate at a predetermined measured temperature, the magnitude of the adjustment being a function of the rate of change of the measured temperature, without attempting to maintain a constant temperature; and
substantially reducing the power supplied to the tissue coagulation apparatus when the measured temperature is at least equal to an input safety temperature.

15. A method as claimed in claim 14, wherein adjusting the fluid flow rate comprises either increasing the fluid flow rate or decreasing the fluid flow rate.

* * * * *

UNITED STATES PATENT AND TRADEMARK OFFICE
CERTIFICATE OF CORRECTION

PATENT NO. : 8,702,693 B2  
APPLICATION NO. : 12/705886  
DATED : April 22, 2014  
INVENTOR(S) : Raj Subramaniam et al.

Page 1 of 1

It is certified that error appears in the above-identified patent and that said Letters Patent is hereby corrected as shown below:

In the Specification

Column 6  
Line 32: after "about 40° C" delete "."  
Line 34: after "65° C" delete "."

Column 7  
Line 1: after "45° C" delete "."  
Line 12: after "+0.2° C" delete "."  
Line 13: after "temperature is 55° C" delete "."  
Line 14: after "temperature is 35° C" delete "."  
Line 32: after "e.g. at 55° C" delete "."  
Line 32: after "with a -0.3° C" delete "."  
Line 36: after "e.g. at 30° C" delete "."  
Line 36: after "and a +0.1° C" delete "."

Signed and Sealed this  
Twenty-second Day of July, 2014

Michelle K. Lee  
*Deputy Director of the United States Patent and Trademark Office*